United States Patent [19]

Nishikawa et al.

[11] Patent Number: 5,093,852
[45] Date of Patent: Mar. 3, 1992

[54] MEDICAL PANORAMIC RADIOGRAPHING DEVICE

[75] Inventors: Kazuo Nishikawa; Kozo Nakano; Keisuke Mori; Takahiro Yoshimura, all of Kyoto, Japan

[73] Assignee: Kabushiki Kaisha Morita Seisakusho, Kyoto, Japan

[21] Appl. No.: 703,596

[22] Filed: May 20, 1991

Related U.S. Application Data

[63] Continuation of Ser. No. 426,745, Oct. 24, 1989, abandoned.

[30] Foreign Application Priority Data

Nov. 8, 1988 [JP] Japan .................................. 63-282297

[51] Int. Cl.⁵ .............................................. A61B 6/14
[52] U.S. Cl. ........................................ 378/39; 378/38; 378/177; 378/175
[58] Field of Search ..................... 378/38, 39, 40, 151, 378/172, 177, 181, 191, 193, 197, 195, 175

[56] References Cited

U.S. PATENT DOCUMENTS

| | | | |
|---|---|---|---|
| 4,286,163 | 8/1981 | Suzuki | 378/40 |
| 4,589,121 | 5/1986 | Makino | 378/40 |
| 4,599,739 | 7/1986 | Nishikawa et al. | 378/39 |
| 4,847,881 | 7/1989 | Heubeck | 378/38 |
| 4,856,038 | 8/1989 | Guenther et al. | 378/40 |
| 4,870,673 | 9/1989 | Adler et al. | 378/38 |
| 4,907,251 | 3/1990 | Mork et al. | 378/38 |

*Primary Examiner*—Janice A. Howell
*Assistant Examiner*—Don Wong
*Attorney, Agent, or Firm*—Koda and Androlia

[57] ABSTRACT

A medical panoramic radiographing device comprises in combination a mode selector which is used to select the panoramic radiographing mode, jaw joint radiographing mode and/or otolaryngological region radiographing mode, an X-ray irradiation timing determination means which is used to determine the X-ray irradiation timing appropriate to the rotation positon of a rotary arm in the sselected radiographing mode, and an X-ray film movement pattern determinator which is used to determine movement patterns regarding the movement timing, speed, etc. of an X-ray film depending on the selected radiographing mode. With this device, the X-ray irradiation timing values or the X-ray film movement timing values suited for various radiographing modes are set automatically to ensure systematic selection of various radiographing modes.

3 Claims, 15 Drawing Sheets

| RIGHT SIDE WHEN CLOSED | RIGHT SIDE WHEN OPENED | LEFT SIDE WHEN OPENED | LEFT SIDE WHEN CLOSED |

FIG.4(c)
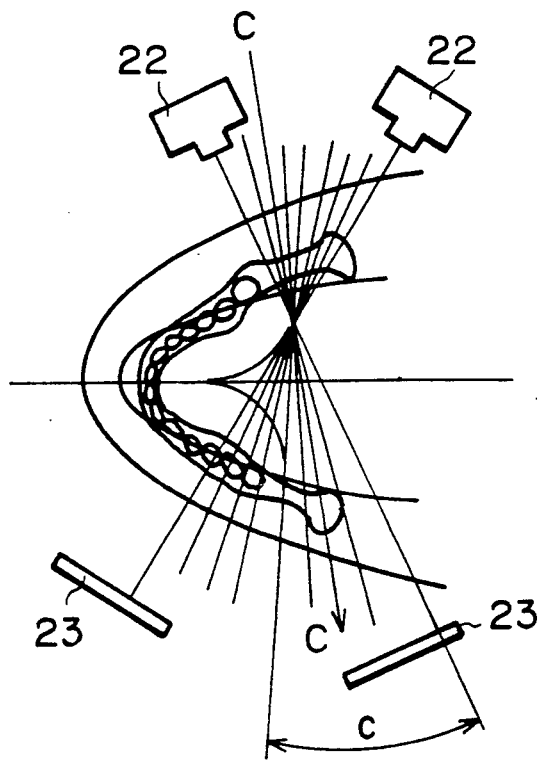
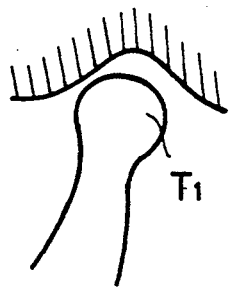
FIG.5(a)
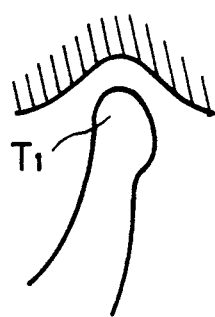
FIG.5(b)
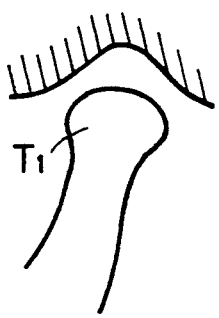
FIG.5(c)

MEDICAL PANORAMIC RADIOGRAPHING DEVICE

This is a continuation of application Ser. No. 426,745, filed Oct. 24, 1989 now abandoned.

1. Field of the Invention

The present invention relates to a medical panoramic radiographing device wherein a jaw joint radiographing means and/or an otolaryngological region radiographing means are added to and systematically integrated with a panoramic radiographing device.

2. Prior Art

A medical panoramic radiographing device (hereinafter a dental panoramic radiographing device is taken as an example) is used to take tomographic radiographs of a patient's dental arch, ranging from a jaw joint on one side, a molar tooth section, a front tooth section and another molar section to a jaw joint on the other side, on a single film. An example of the device will be explained below referring to FIG. 1 which shows an embodiment of the present invention. The device is comprised of a panoramic radiographing main body 1, a horizontal rotary arm 21 which is supported by the main body 1 to rotate horizontally, an X-ray source 22 which is held at one end of the arm 21, an X-ray film holder 23 which includes an X-ray film 231 and is held at the other end of the arm 21 in an opposed relation with respect to the X-ray source 22, an X-ray tomography mechanism 2 which irradiates an X-ray beam from the X-ray source 22 to the X-ray film 231 in a substantially perpendicular direction while the movement speed of the X-ray source 22 is synchronous with that of the X-ray film 231 as the rotary arm 21 rotates, and a patient positioning means 3 which is disposed between the X-ray source 22 and the film holder 23.

With the above-mentioned dental panoramic radiographing device, the tomography mechanism 2 rotates around the head of the patient which is held by the patient positioning means 3 and the X-ray beam is irradiated from the X-ray source 22 to the dental arch of the patient. The images of the dental arch are projected on the X-ray film 231 one after another. If the rotation range of the rotary arm 21 is restricted and if the X-ray is irradiated only in the restricted range, it is possible to take curved tomographic radiographs of the jaw joints or otolaryngological region.

These days, curved tomographic radiography information regarding the jaw joints and otolaryngological region has become highly evaluated for dental and otolaryngological treatments. The dental panoramic radiographing device has become to be frequently used for radiographing the jaw joints and otolaryngological region.

When the dental panoramic radiographing device is used for radiographing the jaw joints and otolaryngological region, the setting of the proper rotation range of the rotary arm, the setting of the X-ray irradiation timing and the setting of the X-ray film movement timing are required to be determined by the operator depending on his eyesight and intuition. Such operations are troublesome and the accuracy of radiographing inevitably depends on the difference among individual operators. In addition, since the incidence angle of the X-ray beam to the jaw joints is constant, only one type of tomographic image information is obtained even if the right and left images of the opened and closed conditions of the jaw joints are taken on a film by divided radiographing and panoramic processing. Therefore the information is insufficient as judgment data for formation abnormality and other deficits, although it is possible to check the positional change of a joint projection by comparison.

SUMMARY OF THE INVENTION

Accordingly the purpose of the present invention is to provide a novel medical panoramic radiographing device by adding a jaw joint or otolaryngological region radiographing mode selection means to a conventional dental panoramic radiographing device so that the X-ray irradiation timing and the movement timing of an X-ray film suited for such radiographing modes can be set automatically. The radiographing modes can be selected systematically to eliminate troublesome operations and to improve the radiographing accuracy. In addition, the incidence angle of the X-ray beam to the jaw joint is made variable to enhance the diagnostic value of obtained images.

The structure of the present invention will be detailed below referring to the attached drawings of a dental panoramic radiographing device.

BRIEF DESCRIPTION OF THE DRAWINGS

FIGS. 4(a), 4(b), and 4(c) illustrate various patterns of X-ray irradiation angles;

FIGS. 5(a), 5(b) and 5(c) are magnified views illustrating the radiographed jaw joint images corresponding to the patterns shown on FIGS. 4(a), 4(b) and 4(c);

DETAILED DESCRIPTION OF THE INVENTION

Figure 1:
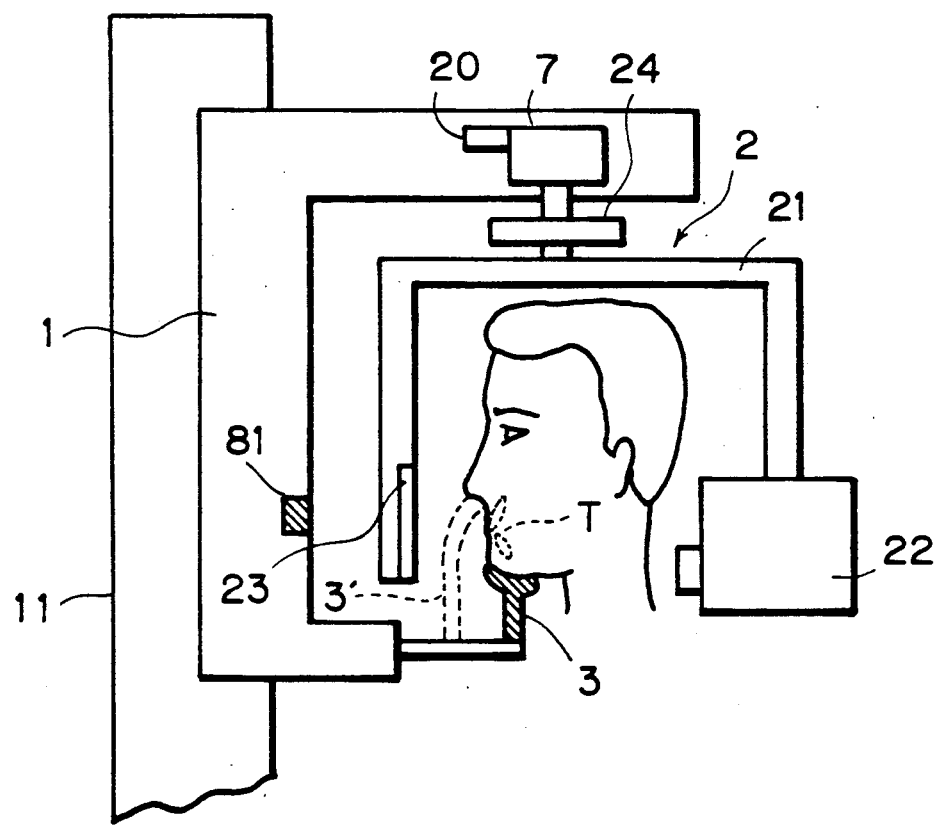
FIG. 1 is a schematic side view of an example of the dental panoramic radiographing device of the present invention.

The dental panoramic radiographing device comprises a panoramic radiographing main body 1, a horizontal rotary arm 21 which is supported by the main body 1 to rotate horizontally, an X-ray source 22 which is held at one end of the arm 21, an X-ray film holder 23 which includes an X-ray film 231 and is held at the other end of the arm 21 in an opposed relation with respect to the X-ray source 22, an X-ray tomography mechanism 2 which irradiates an X-ray beam from the X-ray source 22 to the X-ray film 231 in a substantially perpendicular direction while the movement speed of the X-ray source 22 is synchronous with that of the X-ray film 231 as the rotary arm 21 rotates, and a patient positioning means 3 which is disposed between the X-ray source 22 and the film holder 23, the device being characterized in that the device further comprises a radiographing mode selection means 4 which is used to select the panoramic radiographing mode or the jaw joint radiographing mode and/or the otolaryngological region radiographing mode, an X-ray irradiation timing determination means 5 which is used to determine the X-ray irradiation timing appropriate to the rotation position of the rotary arm 21 in the selected radiographing mode, and an X-ray film movement pattern determination means 6 which is used to determine the appropriate movement pattern regarding the movement timing, speed, etc. of the X-ray film 231 in the radiographing mode selected by the selection means 4.

The dental panoramic radiographing device which is the subject matter to be solved by the present invention comprises a support 11, a panoramic radiographing main body 1 installed on and vertically adjustable along the support 11, a horizontally rotatable tomography mechanism 2 suspended from the main body 1, and the patient positioning means 3 disposed in the rotation locus area of the tomography mechanism 2.

As described above, the tomography mechanism 2 includes the horizontal rotary arm 21, the X-ray source 22 held at one end of the rotary arm 21 and the X-ray film holder 23 held at the other end of the rotary arm 21 in an opposed relation with respect to the X-ray source 22, and a rotary drive mechanism 24 which drives the rotary arm 21 along the path in proportion to the dental arch of the patient being held by the patient positioning means 3. The X-ray source 22 and the X-ray film holder 23 rotate on an approximately elliptical locus along the dental arch so that the curved tomographic radiographs of the dental arch are taken on the X-ray film 231. The rotary drive mechanism 24 is structured using various known mechanisms so that the rotary arm 21 rotates on such an approximately elliptical locus.

The radiographing mode selection means 4 includes a display unit (not shown) and a command input keyboard 42 and used to select the panoramic radiographing mode or the jaw joint radiographing mode and/or the otolaryngological region radiographing mode. From the keyboard 42, a selection command signal is input to a microprocessor 56 (FIG. 2) on the main body to control the X-ray irradiation timing determination means 5 and the X-ray film movement pattern determination means 6.

The X-ray irradiation timing determination means 5 determines the X-ray irradiation timing appropriate to the selected radiographing mode. In the panoramic radiographing mode, the irradiation timing is determined as described below. When or just before the rotary arm 21 begins to rotate, the X-ray source 22 is turned on. When or just after the rotary arm 21 stops rotating, the X-ray source 22 is turned off. In the jaw joint radiographing mode, the irradiation timing is determined so that the X-ray source 22 is turned on only when the rotary arm 21 rotates in the right and left jaw joint regions.

These irradiation timings have been programmed in the microprocessor 56 as numerous patterns corresponding to the above-mentioned radiographing modes. One of the patterns is selected by a radiographing mode selection signal. According to the selected pattern, the on/off timing of the X-ray irradiation source 22 is controlled. When performing divided radiographing of the jaw joint or otolaryngological region on an X-ray film, the slow start portion generated when X-ray irradiation begins can be canceled by setting the X-ray irradiation timing slightly earlier than the drive start timing of the X-ray film holder 23. The boundaries of the divided radiographing section can thus be clarified.

The X-ray film movement pattern determination means 6 determines the movement timing or speed of the X-ray film 231 appropriate to the selected radiographing mode. These movement patterns have also been programmed in the microprocessor 56. One of the patterns is selected by the input signal used in the selected radiographing mode and is input to the movement means 233 of the X-ray film 231 so that the X-ray film 231 moves at the desired timing and speed. A movement pattern used in the panoramic radiographing mode is described below as an example. The X-ray film 231 begins to move just when or slightly after the rotary arm 21 begins to rotate. The X-ray film 231 then continuously moves at the same speed as the rotation speed of the rotary arm 21. When the rotary arm 21 stops rotating, the X-ray film 231 moves by one sheet length and stops. In the jaw joint or otolaryngological region radiographing mode, the X-ray film 231 moves according to a programmed movement pattern. Before the next irradiation begins, the X-ray film 231 is fed quickly and stands by or just remains stopped so that the images of various portions can be radiographed at the desired positions of the X-ray film 231.

It is desirable that the tomography mechanism 2 and/or patient positioning means 3 are movable back and forth by the moving mechanism 7. The patient and the tomography mechanism 2 can thus be positioned properly depending on the panoramic radiographing mode or jaw joint radiographing mode and/or otolaryngological region radiographing mode. Particularly in the panoramic radiographing mode, the moving mechanism 7 functions so that the dental arch of the patient coincides with the tomography region drawn by the tomography mechanism 2. In the jaw joint radiographing mode or otolaryngological region radiographing mode, the X-ray irradiation angle to the portion to be radiographed can be changed. The moving mechanism 7 moves the tomography mechanism 2 and/or patient positioning means 3 back and forth by an appropriate distance depending on the radiographing mode selected by the radiographing mode selection means 4. In addition, it is possible to provide a back-and-forth movement distance determination means 8 between the radiographing mode selection means 4 and the moving mechanism 7. The back-and-forth movement distance determination means 8 determines the proper movement distance of the moving mechanism 7 so that the moving mechanism 7 moves according to the determination input signal of the determination means 8.

The back-and-forth movement distance determination means 8 compares the detection position data obtained by a position detection sensor 81, means 3 to the panoramic radiographing main body with the relative position data of the tomographic region drawn by the tomography mechanism 2 to the panoramic radiographing main body 1. The means 8 then generates a command signal to the moving mechanism 7. The position detection sensor 81 detects the position of the patient's head being held by the patient positioning means 3 and outputs the relative position data of the patient's dental arch to the imaginary reference position of the panoramic radiographing main body 1. The sensor 81 is disposed outside the tomography mechanism 2 or the rotation locus of the tomography mechanism 2 and installed at a proper position along the medial line of the patient. The sensor 81 detects the visible light, laser light or infrared light irradiated to and reflected from the dental arch (front or canine tooth region), lips or cheeks of the patient. An optical distance measurement sensor or a supersonic measurement distance sensor or an optical phase difference detection sensor can be used as the position detection sensor 81. The reference installation position of the sensor 81 can be at any fixed portion of the radiographing device. The most appropriate position is on the medial line of the patient. The above-mentioned tomographic region means a region to be radiographed by tomographic method along the dental arch of the patient using the tomography mechanism 2. The tomographic region is fixed and set to the device. In addition to the fixed region, some typical models are created from among many statistically collected dental arch shape data and input beforehand in a comparator circuit 82 described later. The models are selectively output and compared with the data detected by the sensor 81. In the former case, the difference between the position data detected by the sensor 81 is directly input into the drive circuit 71 of the moving mechanism 7. The tomography mechanism 2 and/or the patient positioning means 3 are moved and positioned properly by the moving mechanism 7. In the latter case, the operator checks the shape of the dental arch of the patient and selects a proper model from among the above-mentioned models. The selection is performed through the command input keyboard 841 to the patient positioning control microprocessor 84.

The selected tomographic region is compared with the data detected by the sensor 81 so that the patient can be positioned properly. This kind of the patient positioning method is mainly used for panoramic radiographing. In the jaw joint or otolaryngological region radiographing mode, it is also possible to properly position the patient by moving the tomography mechanism 2 and/or the patient positioning means 3 depending on the corresponding radiographing mode selection signal. After selecting one of the above-mentioned radiographing modes, the operator operates the patient position control keyboard 841. Automatic positioning is thus performed depending on the selected radiographing mode. The drive circuit 71 receives commands from the sensor 81 or the comparator 82 and generates signals to move the tomography mechanism 2 and/or the patient positioning means 3 to their proper positions. In other words, the drive circuit 71 is connected to the moving mechanism 7 comprising a drive means 71 such as a motor (including a linear motor) or a solenoid. The moving mechanism 7 plays a main role of moving the tomography mechanism 2 and/or the patient positioning means 3 to their proper positions. In this case, it is the most desirable to automatically operate the moving mechanism 7 by directly inputting commands from the drive circuit 71 to the moving mechanism 7. It is, however, possible to manually operate the moving mechanism 7 using a manually-operated ON/OFF circuit.

Furthermore, the radiographing mode selection means 4 includes a selection means 41 for a plurality of X-ray irradiation angles in the jaw joint or otolaryngological region radiographing mode. It is desirable that the command signal from the selection means 41 is input to the moving mechanism 7 or the back-and-forth movement distance determination means 8 and the tomography mechanism 2 and/or the patient positioning means 3 are moved to their proper positions. The selection mode signal of the X-ray irradiation angle selected by the selection means 41 is input to the microprocessor 56 of the main body or the positioning control microprocessor 84. X-ray irradiation angle data has been stored in the microprocessors 56 and 84. The tomography mechanism 2 and/or the patient positioning means 3 are positioned back and forth depending on the selected angle data. In addition to the several kinds of irradiation angle data, continuous data can also be stored in the microprocessors 56 and 84. The angle data is related to the X-ray irradiation timing determination means 5 and the X-ray film movement pattern determination means 6 so that the X-ray irradiation timing and X-ray film movement pattern can be determined depending on the preset irradiation angle.

In the case of the jaw joint or otolaryngological region radiographing, a plurality of divided images are taken on a single film. To prevent overlapping at the boundaries of divided images, it is desirable to provide a position detector 232 on the film holder 23 so that the position detector 232 detects the film position each time the X-ray film 231 moves by the predetermined distance and turns off X-ray irradiation. A limit switch method or a photointerruptor method wherein a photosensor detects the slit of a light shielding plate provided behind the X-ray film 231 is used as the position detector 232.

The general functions of the above-mentioned device are described below referring to FIGS. 1 and 2. First, the radiographing mode selection means 4 selects a desired radiographing mode. When the panoramic radiographing mode is selected, the X-ray irradiation timing and the X-ray film movement pattern suited for panoramic radiographing mode are determined by the X-ray irradiation timing determination means 5 and the X-ray film movement pattern determination means 6. When the radiographing switch is turned on, the rotary arm 21 begins to rotate. The X-ray beam is irradiated from the X-ray source 22 along the dental arch of the patient being held by the patient positioning means 3 according to the above-mentioned irradiation timing. The tomographic radiographing images of the dental arch are taken on the X-ray film 231 which moves in the film holder 23 according to the above-mentioned movement pattern. When the radiographing device is equipped with the moving mechanism 7 and the back-and-forth movement distance determination means 8, the moving mechanism 7 is activated after the panoramic radiographing mode is selected and the patient positioning control keyboard 841 is operated. The tomography mechanism 2 and/or the patient positioning means 3 thus move back and forth so that the dental arch of the patient is automatically aligned with the tomographic region. This patient positioning method is basically identical to that disclosed by the Japanese Patent Application No. 63-58705. The method is used in the present invention without any modifications. When the jaw joint or otolaryngological region radiographing mode is selected, the X-ray irradiation timing and the X-ray film movement pattern suited for the selected radiographing mode are determined in the same manner as described above. According to the determined timing and pattern, the rotary arm 21 rotates, the X-ray is irradiated while the rotary arm 21 passes the intended radiographing region. Images are taken on the predetermined positions of the X-ray film 231 which moves according to the movement pattern. When divided images are taken on the X-ray film 231, the X-ray film 231 is fed rapidly and stopped. This rapid feeding and stopping are repeated while the rotary arm 21 rotates so that X-ray images of various divided portions can be taken on the single X-ray film 231 without overlapping.

An example of the above-mentioned divided radiographing is described below referring to the attached figures. FIG. 3 shows the radiographed images of the open and closed (occluding) conditions of the right and left jaw joints on the single X-ray film 231. When this kind of radiographing mode is selected, the horizontal rotary arm 21 of the tomography mechanism 2 is set at the radiographing start position of the left (right) jaw joint. When the X-ray irradiation switch is turned on, the rotary arm 21 begins to rotate. When the rotary arm 21 reaches a preset position or a positioned determined by calculation, the X-ray source 22 turns on. A moment later, the tomographically radiographed image of the left (right) jaw joint is taken on the X-ray film 231. When the tomographically radiographed image of the left (right) jaw joint is completed, the X-ray source 22 turns off. During the off period, the X-ray film 231 is fed by the ¼ length thereof. The tomographically radiographed image of the left (right) jaw joint is taken in the region between the beginning and ¼ length of the X-ray film 231. After this, the rotary arm 21 rotates and the X-ray film 231 is fed further. When the rotary arm 21 reaches the right (left) jaw joint radiographing start position, the X-ray source 22 turns on to take the tomographic radiographing of the right (left) jaw joint. The image of the right (left) jaw joint is thus taken on the area between 4/4 and ¾ regions of the X-ray film 231. After the radiographing of the right (left) jaw joint, the X-ray source 22 turns off and the rotation of the rotary arm 21 and the feeding of the X-ray film 231 stop. The rotary arm 21 then begins rotating in the reverse direction and the X-ray film 231 is fed in the reverse direction. The rotary arm 21 returns to the start position for radiographing the left (right) jaw joint. At this time, the X-ray film 231 stops so that its ¼ region is to be exposed. When the mouth of the patient is opened and the X-ray irradiation switch is turned on, the rotary arm 21 rotates. When the rotary arm 21 reaches a preset position or a positioned determined by calculation, the X-ray source 22 turns on. A moment later, the X-ray film 231 is begun to be fed and the tomographically radiographed image of the opened left (right) jaw joint is taken on the area between the ¼ and 2/4 regions of the X-ray film 231. When radiographing is completed, the X-ray source 22 turns off. The rotary arm 21 further rotates. When the rotary arm 21 reaches the right (left) jaw joint radiographing start positioned, the X-ray source 22 turns on and the tomographically radiographed image of the right (left) jaw joint is taken. The X-ray film 231 is fed to the 2/4 region thereof and the tomographically radiographed image of the right (left) jaw joint is taken on the area between 2/4 and ¾ regions of the X-ray film 231. As a result, equally divided, tomographically radiographed images of the closed left and right jaw joints are taken on both end regions of the film and those of the opened left and right jaw joints are taken on the central two regions of the film. The above sequence of operation is performed automatically and smoothly according to the radiographing mode data such as the rotation pattern of the rotary arm 21, the on/off timing pattern of the X-ray source 22, the X-ray film feed start/stop timing pattern and the X-ray film feed speed pattern programmed in the microprocessor 56.

Figure 4A:
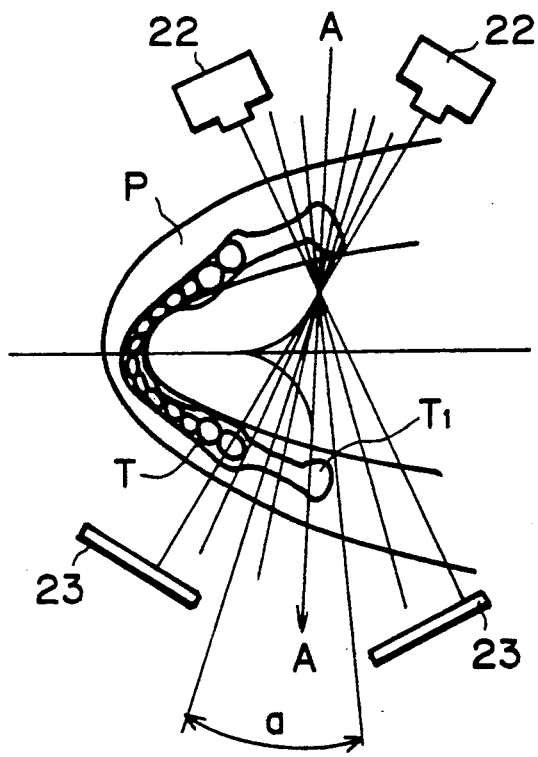
Figure 4B:
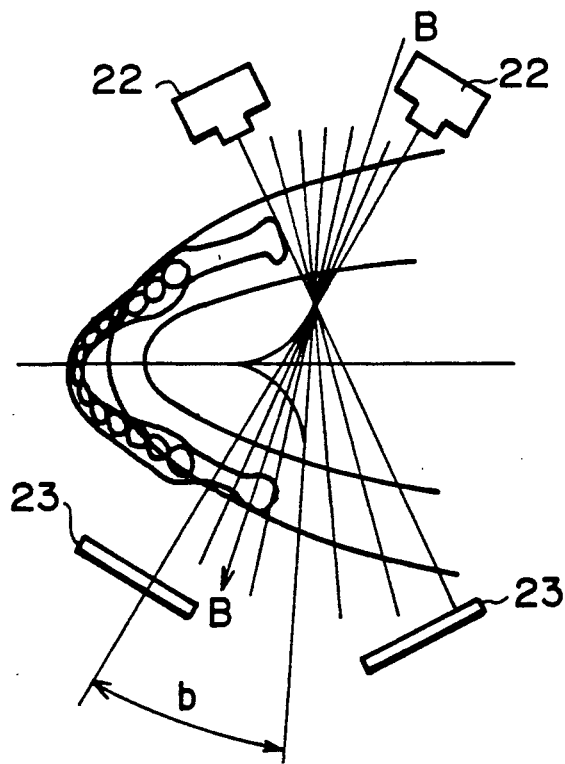
Figure 6:
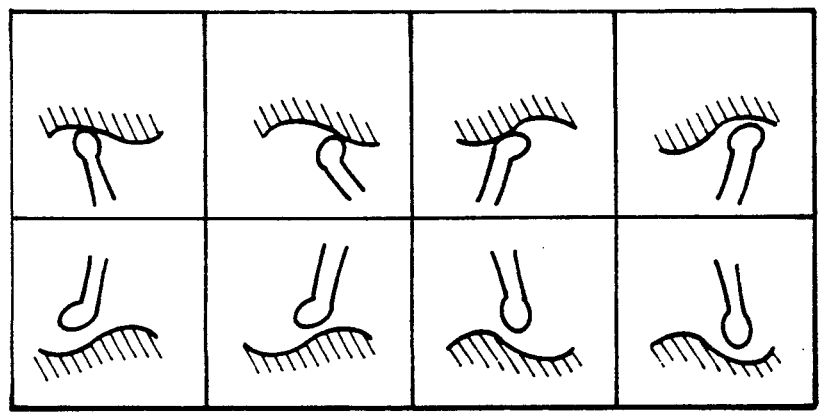
FIG. 6 is a view similar to FIG. 3 and shows an example of numerous images on a film.
Figure 7A:
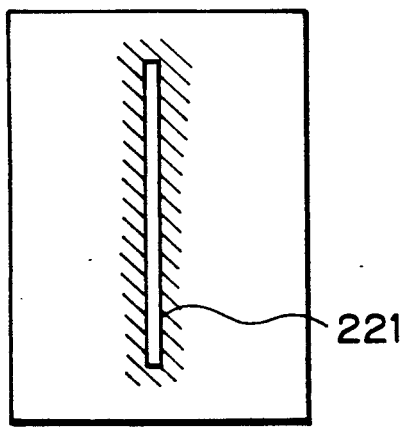
FIGS. 7(a) and 7(b) show examples of slits.
Figure 7B:
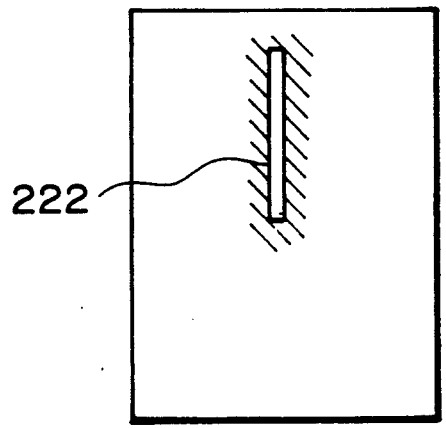

Assume that the radiographing mode selection means 4 has the selection means 41 for selecting a plurality of X-ray irradiation angles used in the jaw joint or otolaryngological region radiographing mode. When the selection means 41 is selected and operated, the corresponding selection mode command signal is input to the moving mechanism 7 and the tomography mechanism 2 and/or the patient positioning means 3 are moved back and forth. The back-and-forth positional relation between the dental arch and tomographic region is thus changed and the X-ray irradiation angle to the object portions to be radiographed is modified. FIG. 4 shows the positional relation between the dental arch and the tomographic region at three incidence angles. Letter T represents the dental arch and letter P represents the tomographic region. FIG. 4(a) shows a condition where the dental arch T almost coincides with the tomographic region P. FIG. 4(b) shows a condition where the dental arch T is slightly projected ahead of the tomographic region P. FIG. 4(c) shows a reverse condition where the tomographic region P is slightly projected ahead of the dental arch T. Letters A, B and C in FIGS. 4(a), 4(b) and 4(c) represent the X-ray irradiation axes extended to the central portion of a joint projection $T_1$. Letters a, b and c represent X-ray irradiation and radiographing ranges. The above-mentioned selection means 41 allows selection of the radiographing mode depending on the X-ray irradiation angle. The selection signal from the selection means 41 is input to the microprocessor 56 or 84 wherein output data has been programmed depending on the radiographing mode. An interlock signal is generated from the microprocessor 56 or 84 to the moving mechanism 7 or the back-and-forth movement distance determination means 8 to move the patient positioning means 3 back and forth as described above. In addition, command signals are input to the X-ray irradiation timing determination means 5 and the X-ray film movement pattern determination means 6 to determine the X-ray irradiation timing and the X-ray film movement pattern depending on the radiographing mode. The above-mentioned programmed output data is used to perform the following sequential operation. In the case of the radiographing mode corresponding to the X-ray incidence angles A, B and C for example, when the X-ray film holder 23 reaches the radiographing region a, b or c, X-ray irradiation is turned on and the X-ray film 231 is begun to be fed. When the X-ray film holder 23 passes the radiographing region a, b or c, the feeding of the X-ray film 231 is stopped. While the rotary arm 21 moves to another radiographing region, the X-ray film 231 is fed further or stopped. The X-ray is irradiated and the movement of the X-ray film 231 is moved again. These irradiation and film movement are conducted sequentially at the incidence angles A, B and C. Using the data, jaw joint images are taken at the three different projection angles on the single X-ray film 231. The jaw joint images taken at the three different incidence angles have different forms as shown in FIG. 5 even when the same jaw joint is radiographed. This means that the joint projection $T_1$ is radiographed at different angles, easily providing much information on diagnosis regarding abnormal forms of the joint projection $T_1$ in the case of a jaw joint disease. FIGS. 5(a), 5(b) and 5(c) correspond to the radiographing modes shown in FIGS. 4(a), 4(b) and 4(c) respectively. FIG. 6 shows a case where a film is divided into eight portions (two divisions in the vertical direction and four divisions in the horizontal direction) and a jaw joint is radiographed in the closed and opened conditions at two different X-ray incidence angles. In this case, the long vertical slit 221 [shown in FIG. 7(a)] for panoramic radiographing disposed ahead of the X-ray source 22 can be switched with an upper portion switching slit 222 shown in FIG. 7(b). When a jaw joint is radiographed in the above-mentioned manner while the slits 221 and 222 are switched, the tomographically radiographed images of the left and right jaw joints in the closed and opened conditions at one of the selected incidence angles are obtained at the upper half of the X-ray film 231. When jaw joint radiographing is performed after the X-ray incidence angle is switched to a different angle, and the X-ray film 231 is turned upside down, the tomographically radiographed images of the left and right jaw joints in the closed and opened conditions at the different incidence angle are obtained at the remaining blank portions of the X-ray film 231. The radiographing directions and jaw joint opening/closing conditions can be combined as desired. Furthermore, the number of divided portions of the X-ray film 231 can be changed as desired by modifying the size or feed speed of the film. The X-ray irradiation angles cannot be limited to the above-mentioned A, B and C, but other angles can be selected continuously as desired. It is possible to analogically control the X-ray irradiation timing and the X-ray film movement pattern depending on the selected angle.

When a plurality of divided images are taken on the single X-ray film 231 as described above, the boundaries of the divided images are prevented from being overlapped using the position detector 232 provided on the X-ray film holder. The position detector 232 detects the position of the X-ray film 231 each time the film is moved by a specified distance. This detection signal is fed back to the moving mechanism 233 of the X-ray film 231 and the control mechanism of the X-ray source 22 to control the X-ray irradiation timing and the film movement timing. As a result, clear images can be obtained to ensure more accurate diagnosis.

The above-mentioned divided radiographing method is also used for radiography of the otolaryngological region. Accurate diagnosis for otolaryngological treatments can be greatly enhanced since various images are taken at different X-ray irradiation angles on the single X-ray film 231.

EMBODIMENTS

The embodiments of the present invention will be detailed below. FIG. 1 is a schematic view of an example of the medical panoramic radiographing device of the present invention. Referring to FIG. 1, the panoramic radiographing main body 1 is supported on the stay 11 and adjustable vertically along the stay 11. The horizontal rotary arm 21 of the tomography mechanism 2 is suspended from the main body 1 via a rotation drive mechanism 24. The horizontal rotary arm 21 can be rotated along the shape of the dental arch T of the patient and can be moved back and forth by the moving mechanism 7 provided in the main body 1. Under the main body 1, two patient positioning means 3 and 3' are provided. The patient positioning means 3 supports the lower section of the patient jaw and is used in the panoramic radiographing mode. The patient positioning means 3' gently supports the lower section of the nostril of the patient and is used in the jaw joint or otolaryngological region radiographing mode. These patient positioning means can be retracted from their predetermined positions and are selectively used depending on the radiographing mode. The reasons for retracting the two patient positioning means 3 and 3' are described below. The lower jaw of the human being moves up and down via the jaw joint. When the opened and closed conditions of the jaw joint are radiographed as described above with the lower jaw secured and supported from below the lower jaw, the jaw joints are moved up and down. This reduces the accuracy of diagnosis since the diagnosis is based on the comparison between the relative positional condition of the opened jaw joint and that of the closed jaw joint. By supporting the nostril section of the patient, only the lower jaw can be moved up and down while the head is secured. Therefore, the jaw joint section is held at a fixed position. When performing panoramic radiographing while the nostril section is held, the patient positioning means 3' located in front of the front tooth section hinders panoramic radiographing, although the patient positioning means 3' does not hinder jaw joint radiographing. If the patient positioning means 3' is made of an X-ray transmission material, panoramic radiographing is possible as a matter of course. Referring to FIG. 1, a distance sensor 81 is provided on the panoramic radiographing main body 1 at a position on the medial line of the patient. The sensor 81 detects the relative position of the front tooth section of the patient's dental arch T to the panoramic radiographing main body 1 and compares the detection results with the relative position data of the tomographic region of the tomography mechanism 2. According to this comparison, the above-mentioned moving mechanism 7 moves the tomography mechanism 2 back and forth to position the patient.

Figure 10:
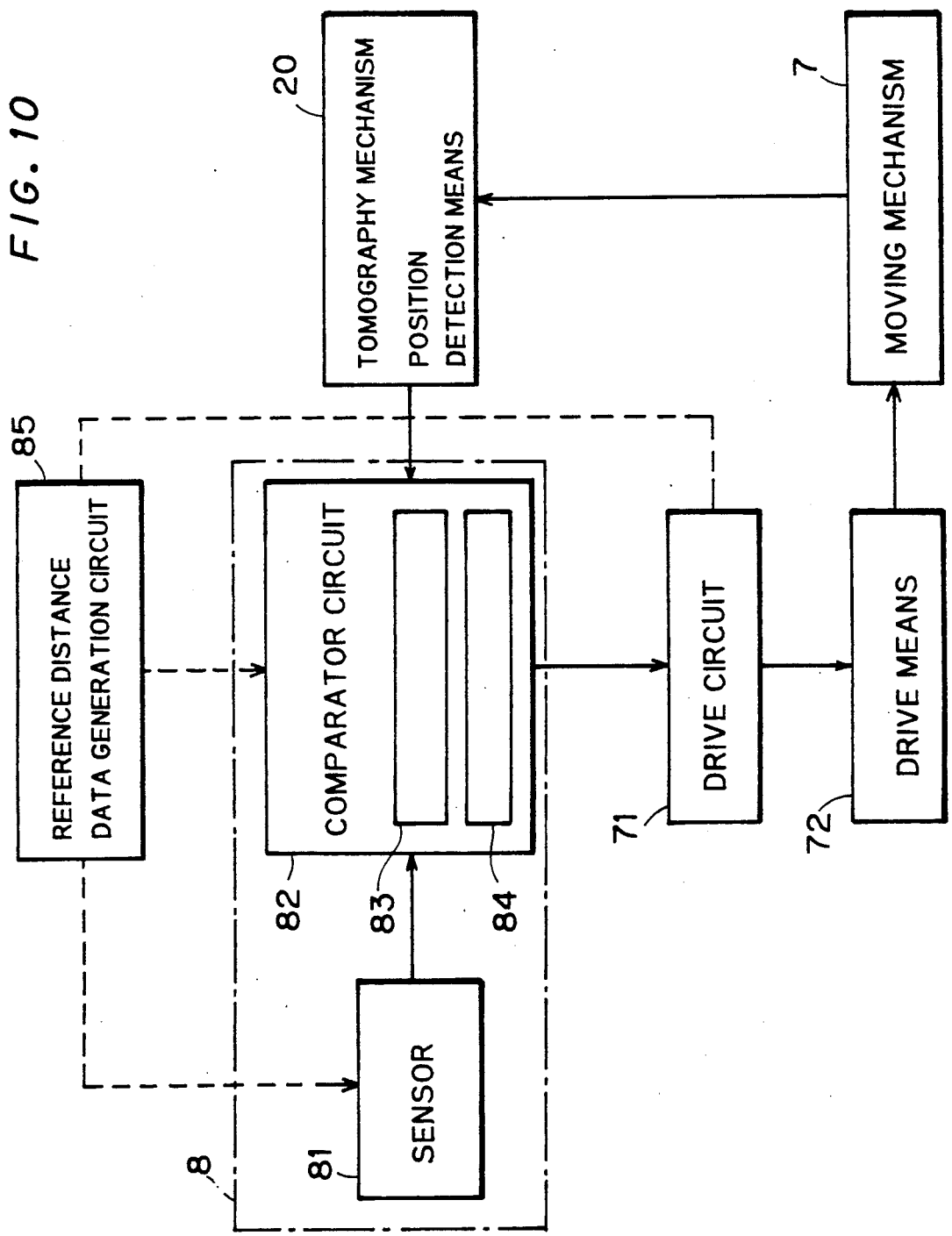
FIG. 10 is a block diagram illustrating the circuitry for panoramic radiographing of the device of the present invention.
Figure 11:
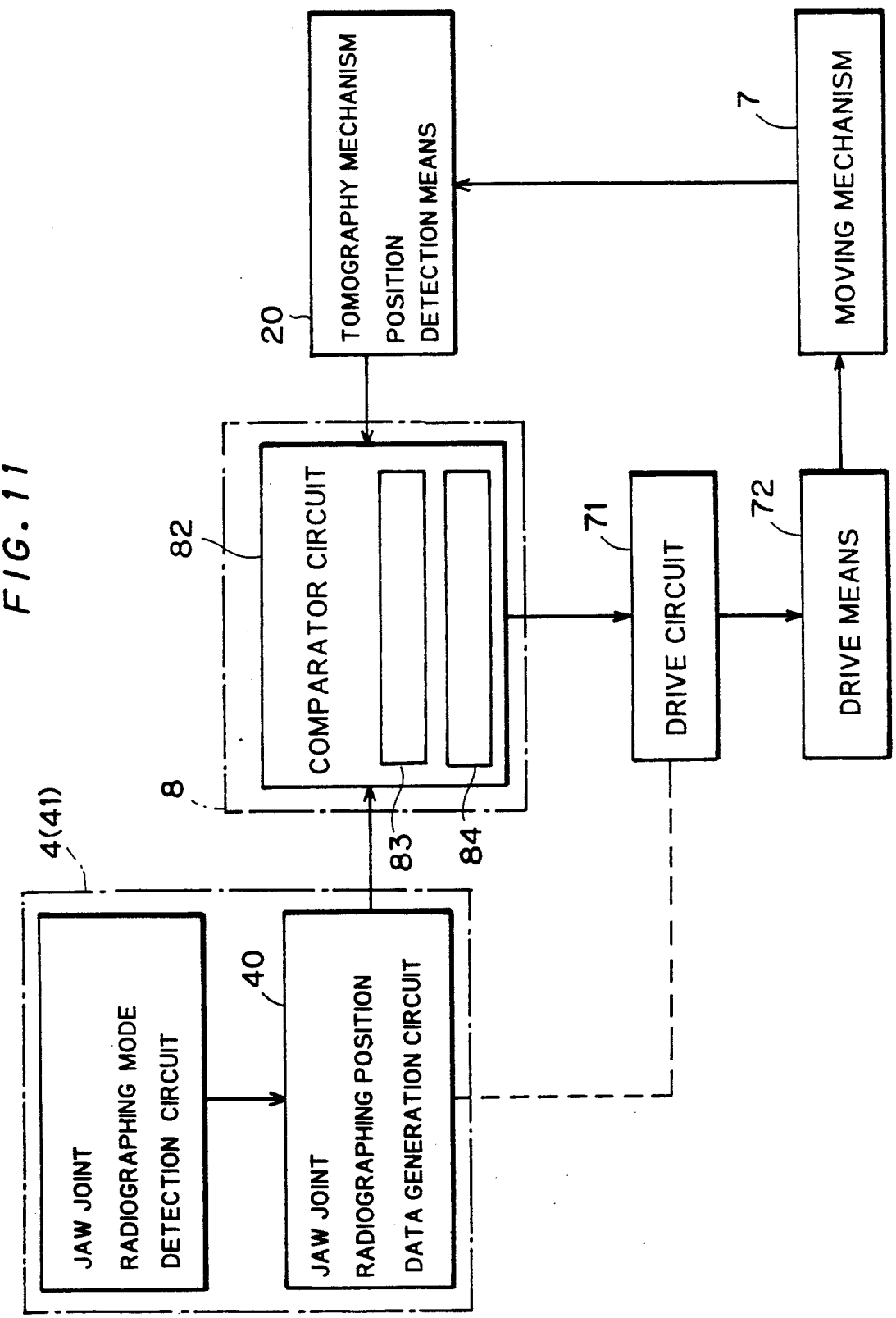
FIG. 11 is a block diagram illustrating the jaw joint-/otolaryngological region radiographing circuitry of the device of the present invention.

FIG. 10 is a circuit block diagram used for patient positioning control in the panoramic radiographing mode. Referring to FIG. 10, the measurement data obtained from the sensor 81 is input to a comparator circuit 82 and compared with the tomographic data obtained from a reference distance data generation circuit 85. The reference distance data generation circuit 85 statistically collects numerous dental arch shapes and creates some typical tomographic models. The model data is input to the comparator circuit 82 each time when required so that the comparator 82 compares the selected tomographic region data with the measurement data obtained by the sensor 81. The reference distance data generation circuit 85 also detects the shape, size and other characteristics (differences among individual patients) of the patient's dental arch. Based on the detection data, the reference distance data generation circuit 85 adjusts the detection position of the sensor 81 beforehand, inputs the reference data for comparison by the comparator circuit 82 and also inputs the proper movement distance of the moving mechanism 7 to the drive circuit 71. It is thus desirable to include the reference distance data generation circuit 85. The comparator circuit 82 includes an A/D converter 83 and the positioning control microprocessor 84. After the command input keyboard 841 (FIG. 2) is operated, the measurement data by the sensor 81 is compared with the tomographic region input data from the reference distance data generation circuit 85. The signal representing the proper movement distance of the tomography mechanism 2 is generated from the microprocessor 84 to the drive circuit 71. The signal is further fed from the drive circuit 71 to the drive means 72. The moving mechanism 7 is thus activated to move the tomography mechanism 2 back and forth. The back-and-forth movement of the tomography mechanism 2 is detected by a tomography mechanism position detection means 20 (FIG. 1) and the detection result is fed back to the comparator 82. This positioning sequence is repeated. FIG. 11 shows a block diagram of the positioning circuit used in the jaw joint or otolaryngological region radiographing mode. When the desired radiographing mode is selected by the radiographing mode selection means 4, the position data suited for the selected radiographing mode is generated from a jaw joint or otolaryngological region radiographing position data generation circuit 40 and inputted to the comparator circuit 82. When radiographing is performed at different X-ray irradiation angles using the selection means 41, the selection mode information of the selection means 41 is also input to the comparator 82. The actual position information of the rotary arm 21 detected by the tomography mechanism position detection means 20 is input to the comparator circuit 82. The above-mentioned position data is compared with the actual position data to determine the proper back-and-forth moving distance of the tomography mechanism 2.

According to the proper movement distance information determined as described above, the moving mechanism 7 is activated by the drive circuit 71 and the drive means 72 so that the tomography mechanism 2 moves back and forth to the position suited for the selected radiographing mode. The movement result of the tomography mechanism 2 is detected by the tomography mechanism position detection means 20, fed back to the comparator 82 in the same manner as described above and corrected to ensure accurate positioning. FIG. 11 also shows a case wherein the position data of the jaw joint or otolaryngological region radiographing position data generation circuit 40 is directly input to the drive circuit 71. This is applicable when moving the rotary arm 21 from its constant predetermined position (for example, the panoramic radiographing start position) in the jaw joint or otolaryngological region radiographing mode to a position where radiographing is performed at a different X-ray irradiation angle.

Figures 2, 3:
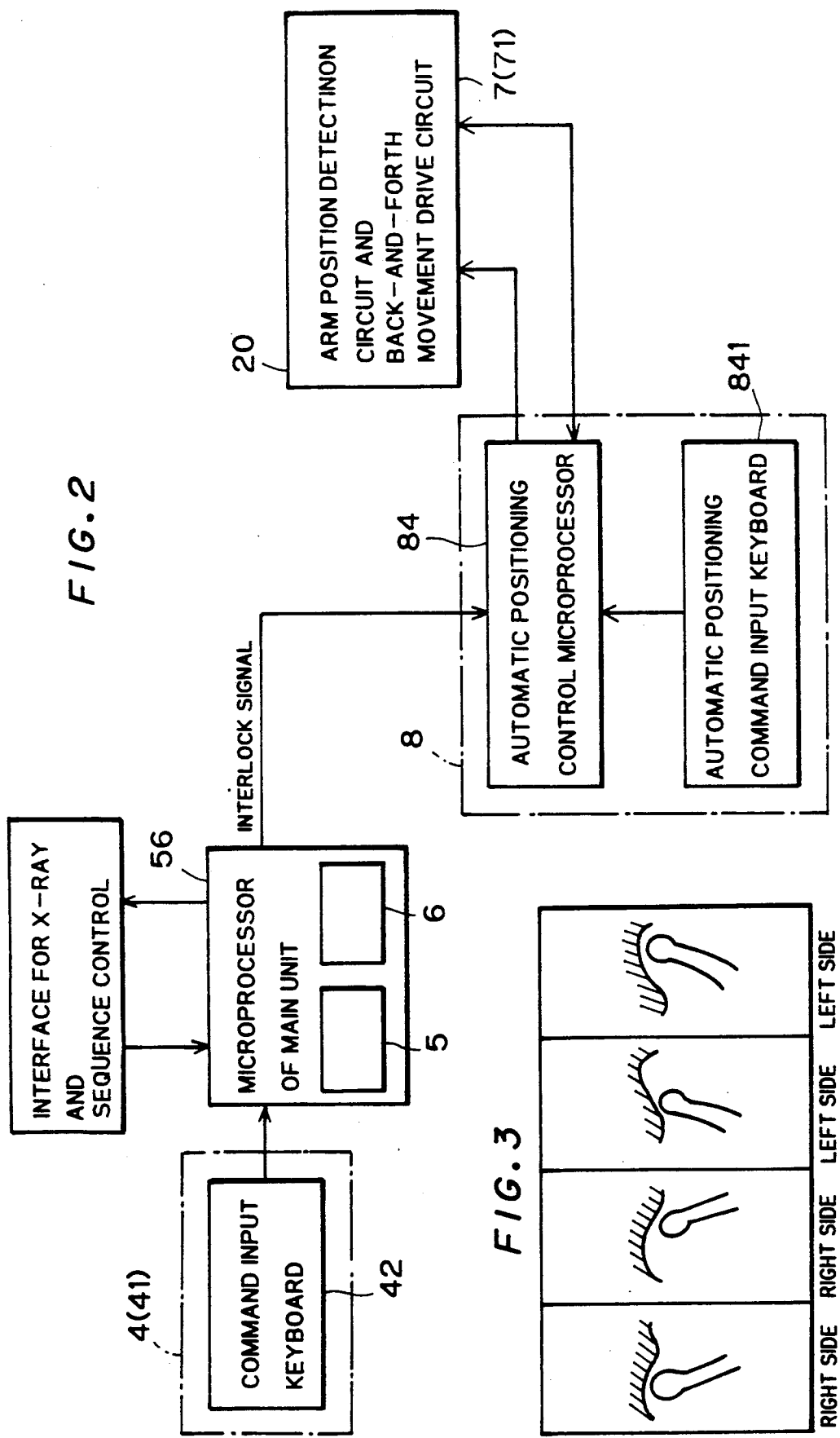
FIG. 2 is a block diagram illustrating the general circuitry of the device.
FIG. 3 illustrates examples of radiographed jaw joint images on a film.

FIG. 2 is a block diagram of a general circuitry including the above-mentioned positioning circuits. Referring to FIG. 2, when the command input keyboard of the radiographing mode selection means 4 (and the selection means 41), the selected mode information is inputted to the microprocessor 56. The X-ray irradiation timing and the X-ray film movement pattern suited for the selected radiographing mode are determined by the X-ray irradiation timing determination means 5 and the X-ray film movement pattern determination means 6. At the same time, an interlock signal is issued to the positioning control microprocessor 84. When the patient positioning command input keyboard 841 is operated, the positioning operation suited for each radiographing mode is performed in the manner as described above. When the radiographing sequence switch is turned on, the desired X-ray curved tomographic radiographing is performed in the selected radiographing mode. In FIG. 2, however, the above-mentioned tomography mechanism position detection means 20 and the moving mechanism 7 are jointed and simply shown as "Arm position detection circuit 20 and back-and-forth movement drive circuit 71."

Figure 8:
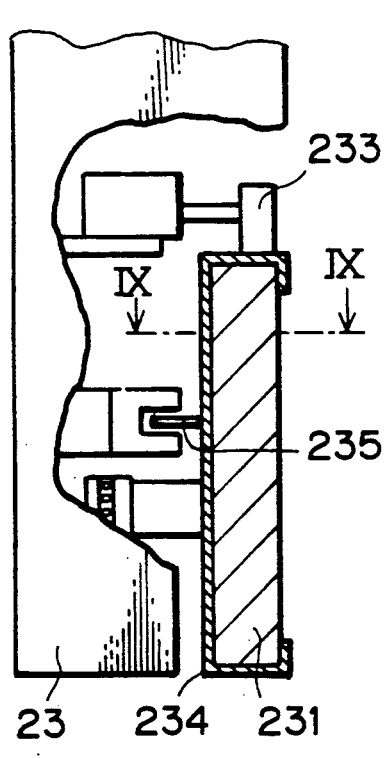
FIG. 8 is a partially cut-away side view illustrating an example of an X-ray film holder.
Figure 9:
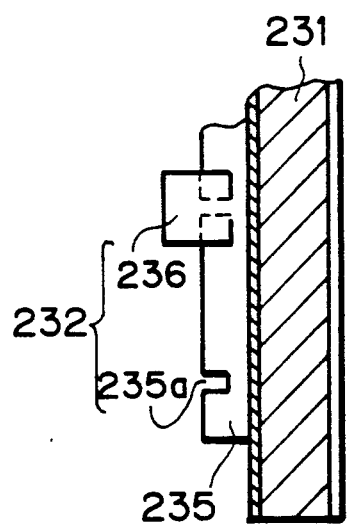
FIG. 9 is a cross-sectional view taken on line IX—IX of FIG. 8.

FIGS. 8 and 9 show a means to prevent the boundaries of divided images taken on the single X-ray film 231 from being overlapped. A film cassette 234 integrated with the X-ray film 231 is held in the X-ray film holder 23 and can be moved right and left by a moving mechanism 233 (motor). A light shield plate 235 with notches 235a provided at specified intervals is disposed behind the film cassette 234. In the holder 23, a photosensor 236 is disposed. As the film cassette 234 is moved, the photosensor 236 detects the notches 235a. This detection information is input to the X-ray irradiation timing determination means 5 and the X-ray film movement pattern determination means 6. The control used to prevent overlapping is performed as described above. The photosensor 236 and the notches 235a are combined to form a photointerruptor-like position detector 232. When the single X-ray film 231 is divided into four divisions, three notches 235a are provided at equal intervals.

Figure 12:
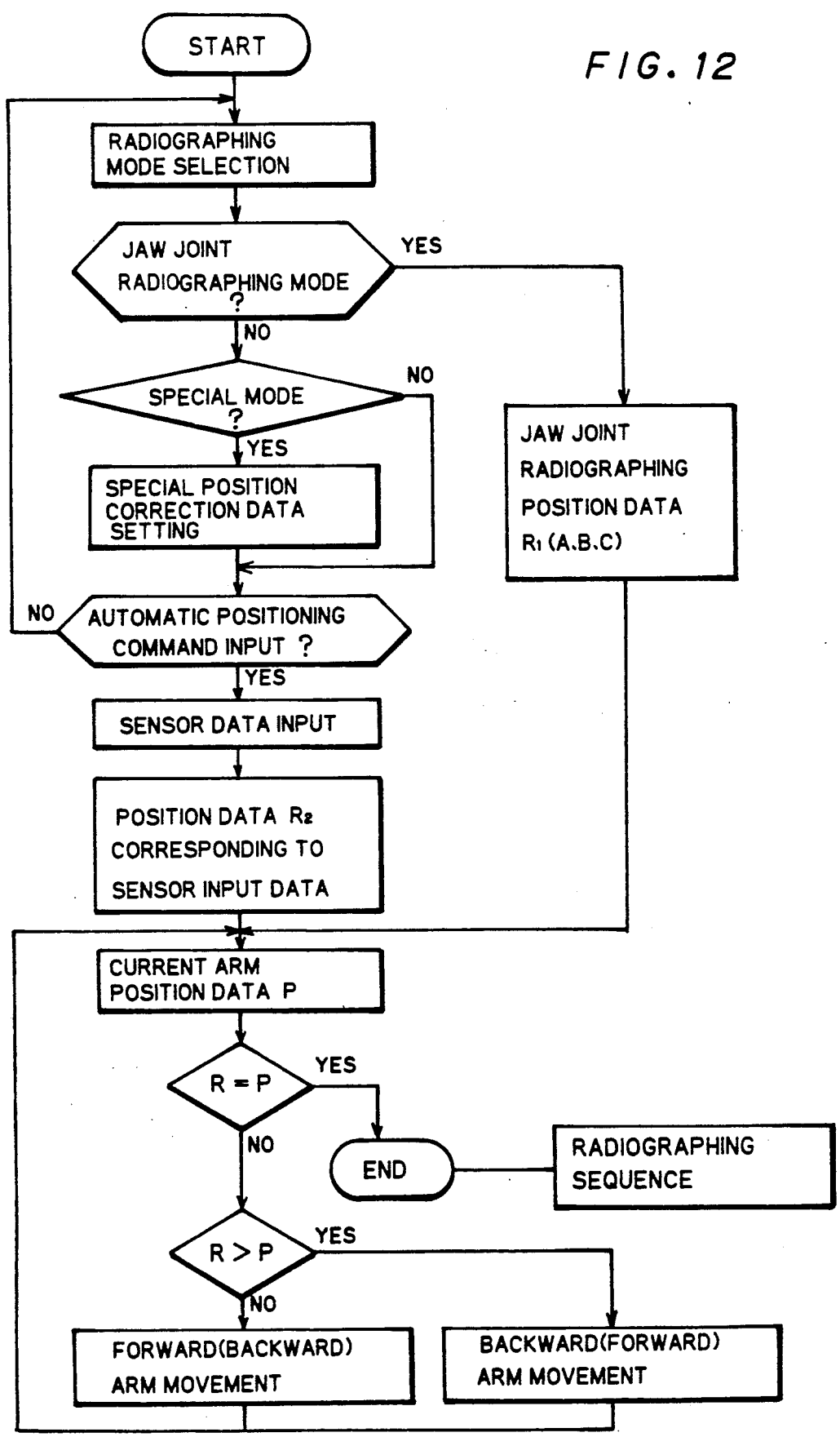
FIGS. 12 to 15 are flowcharts illustrating preparation steps including positional setup operations to be conducted before starting a radiographing sequence.

FIGS. 12 to 15 are flowcharts for preparation steps (including the positioning operation) to be conducted before a radiographing sequence. FIG. 12 shows an example wherein the microprocessor 56 of the main body is used to set different X-ray irradiation angles in the jaw joint or otolaryngological region radiographing mode. First, the start button is pressed and a radiographing mode is selected. When the jaw joint or otolaryngological region radiographing mode is selected, an X-ray irradiation angle is also selected. One piece (A, B, C, . . . ) of the tomography mechanism back-and-forth position data $R_1$ corresponding to a plurality of preset X-ray irradiation angles is selected. The selected position data $R_1$ is compared with the actual position data P of the rotary arm 21. When $R_1 = P$, positioning in the jaw joint or otolaryngological region radiographing mode is completed. If $R_1$ is not equal to P, a movement signal is issued to move the rotary arm 21 forward or backward and $R_1$ is compared with P again. Until they coincide with each other, the movement and comparison are repeated. The positioning is then completed. When a radiographing mode other than the jaw angle or otolaryngological region radiographing mode is selected, selection of a special mode is required in the case of the example shown in FIG. 12. This special mode is used to perform panoramic radiographing of the upper jaw cavity (maxillary bone cavity) for example. If the special mode is not selected, the entire jaw panoramic radiographing mode (the inherent mode of the radiographing device) is selected. If automatic positioning commands are not input after the entire jaw panoramic radiographing mode is selected, the control of the sequence returns to the radiographing mode selection step. If automatic positioning commands are input, sensor data is input and the patient's dental arch position data $R_2$ is calculated. The position data $R_2$ is compared with the actual position data P of the rotary arm 21. The position of the rotary arm 21 is then corrected in the same manner as described above. This completes the positioning operation in the panoramic radiographing mode. If the special mode is selected, special position correction data is set before the automatic positioning command input is turned on. The special position, for example in the case of radiographing the upper jaw cavity, differs from the position used in the entire jaw panoramic radiographing mode by a constant amount obtained by statistical calculation. The above-mentioned setting of the position correction data is done to correct the difference. The rotary arm 21 is moved in the manner described above and positioned at the proper position suited for the radiographing in the special mode. After the positioning is completed, the control enters the sequence of the selected radiographing mode.

Figure 13:
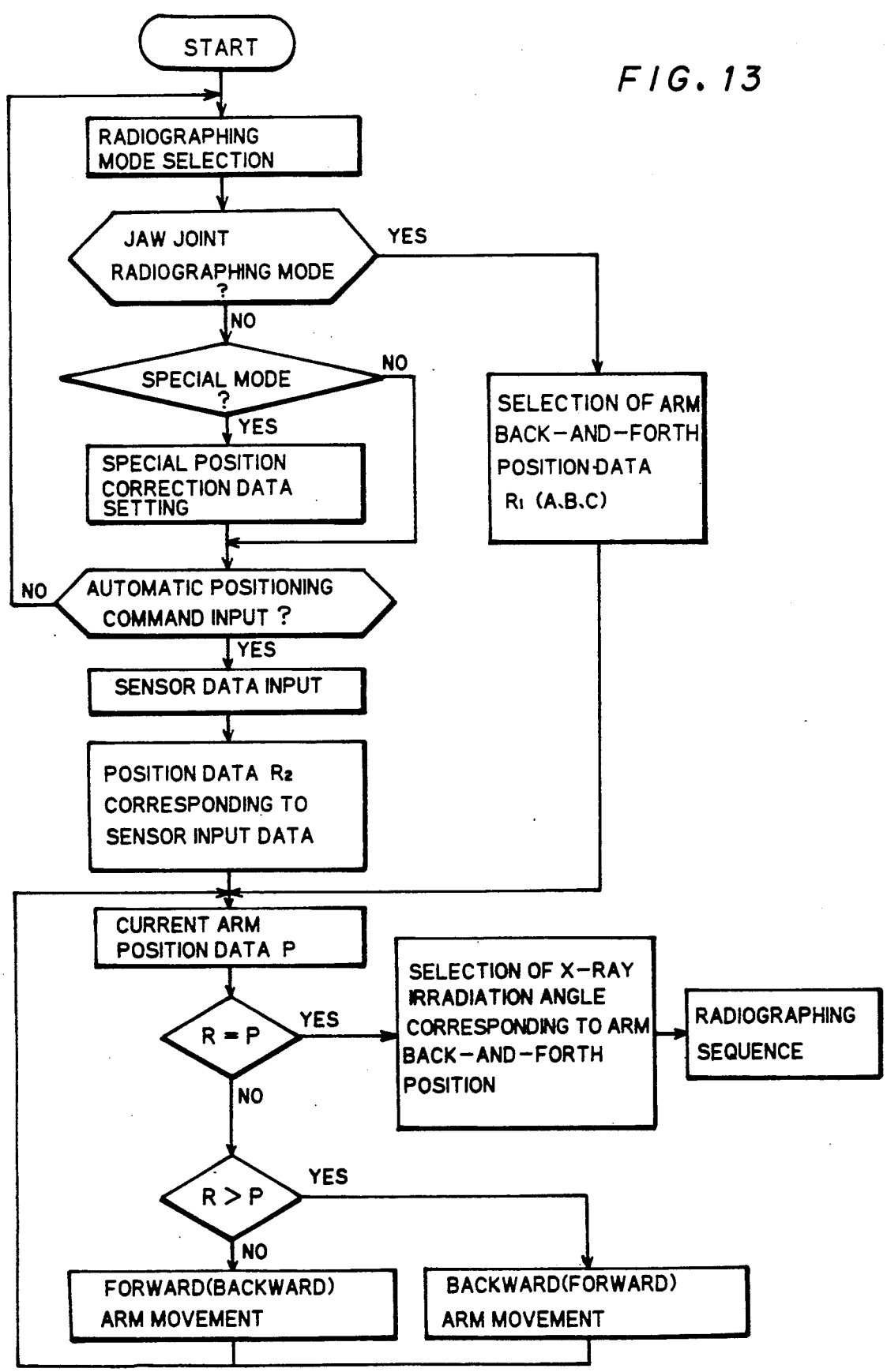

FIG. 13 is a flowchart wherein the microprocessor 84 for automatic positioning control is used to set different X-ray irradiation angles in the jaw joint or otolaryngological region radiographing mode. In the case of this example, the jaw joint or otolaryngological region radiographing mode is selected. The programmed back-and-forth position data $R_1$ (A, B, C) of the rotary arm 21 is selected and compared with the actual position data P to adjust the position of the rotary arm 21. The X-ray irradiation angle corresponding to the position data $R_1$ is then selected. The control then enters the radiographing sequence. Other flowchart patterns are similar to those described above and not detailed here.

Figure 14:
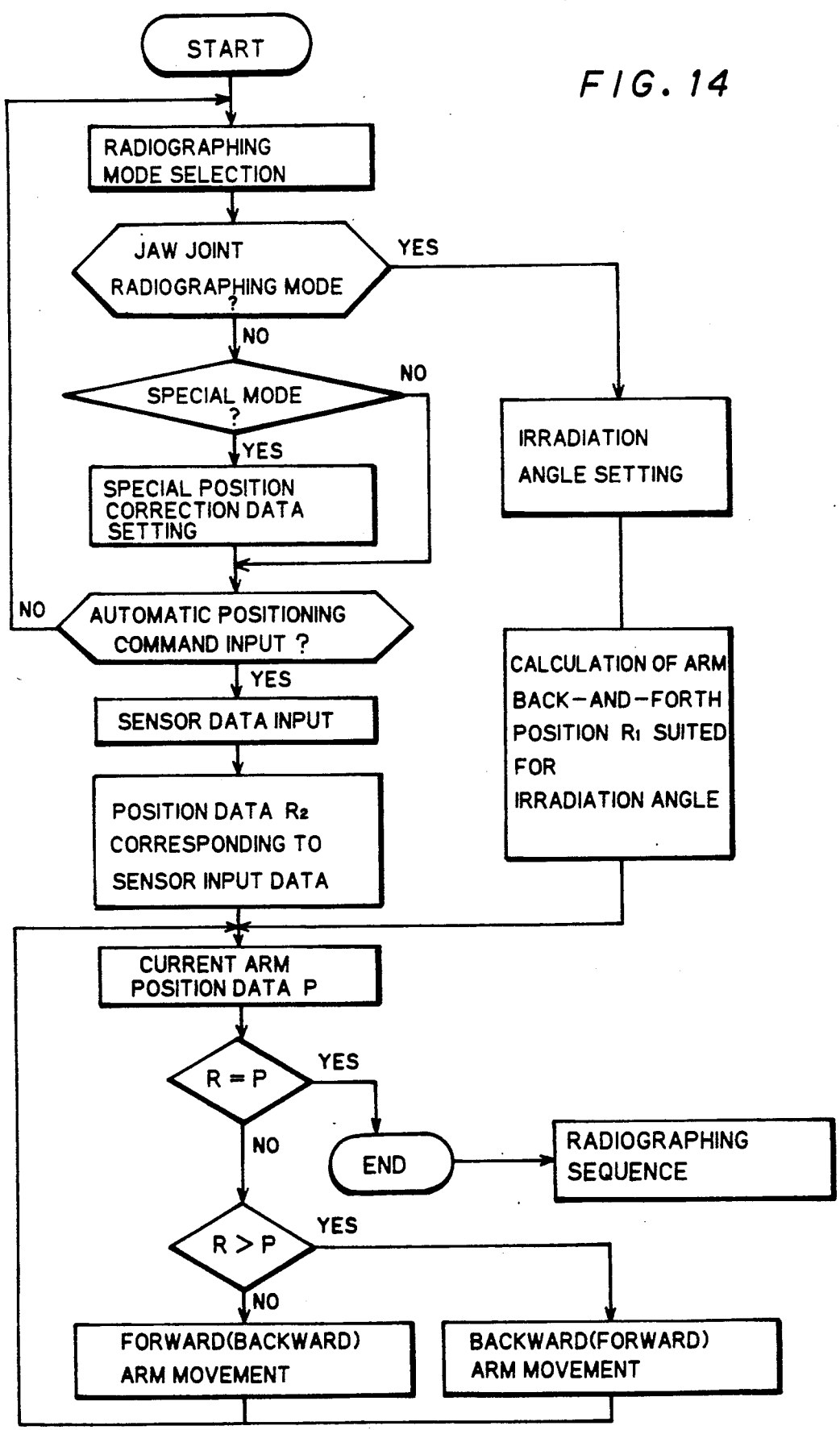

FIG. 14 is a flowchart wherein the microprocessor 56 of the main body is used to continuously set the different irradiation angles in the jaw joint or otolaryngological region radiographing mode. In the case of the example shown in FIG. 13, the number of the X-ray irradiation angles is limited to several, such as A, B and C, and one of these is selected. In the case of the example shown in FIG. 14, the proper back-and-forth position of the rotary arm 21 is calculated depending on a selected angle and the rotary arm 21 is moved back and forth according to the calculated data. Therefore, when an X-ray irradiation angle is selected after the jaw joint or otolaryngological region radiographing mode is selected, the back-and-forth position $R_1$ of the rotary arm 21 corresponding to the X-ray irradiation angle is calculated. The position data $R_1$ is compared with the actual position data P of the rotary arm 21 and the rotary arm 21 is positioned properly. The control then enters the radiographing sequence. Other flowchart patterns are similar to those described above and not detailed here.

Figure 15:
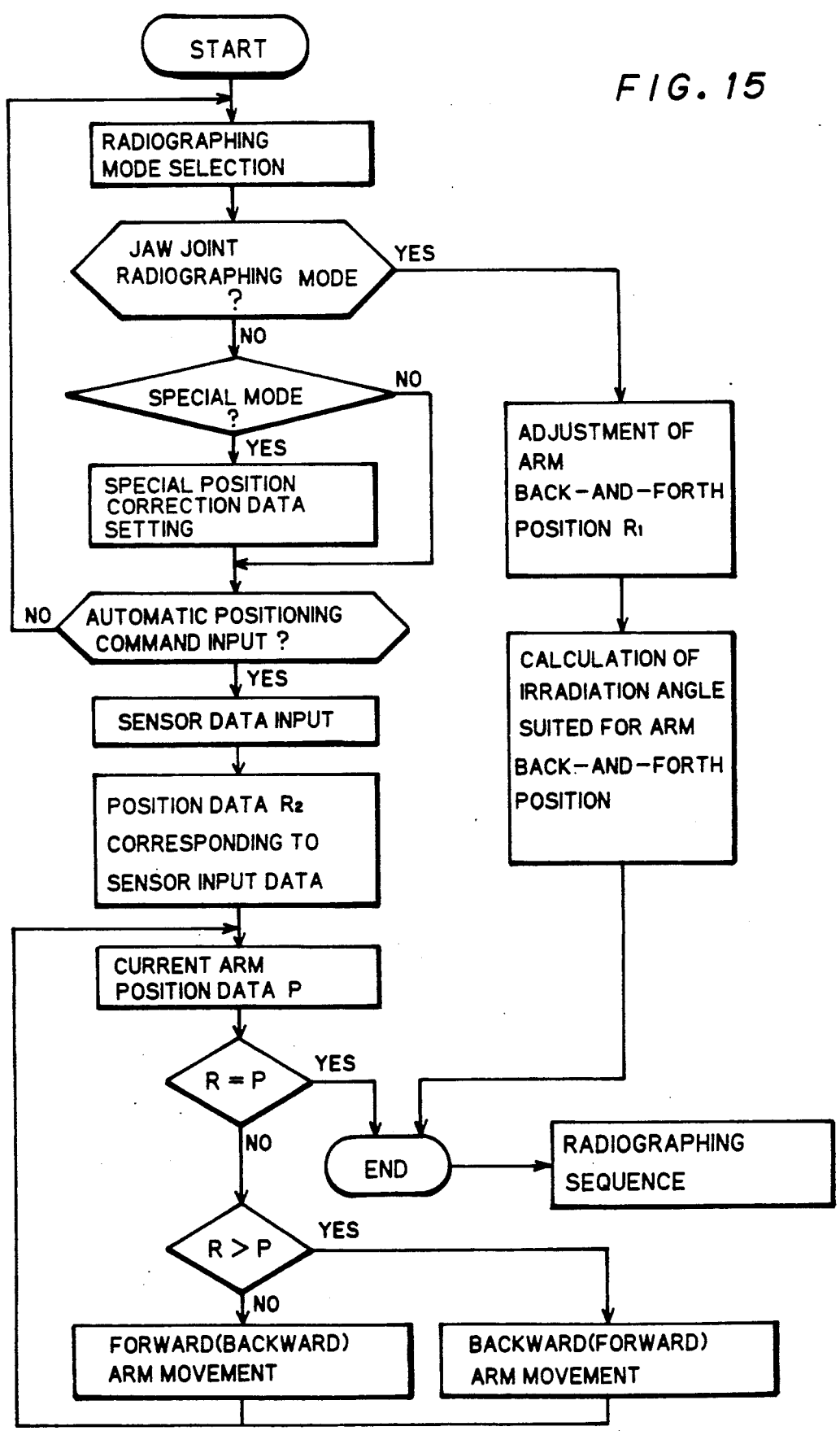

FIG. 15 is a flowchart wherein the microprocessor 84 for positioning control is used to set different irradiation angles in the jaw joint or otolaryngological region radiographing mode by calculation using a desired back-and-forth position of the rotary arm 21. When the jaw joint or otolaryngological region radiographing mode is selected, the rotary arm 21 is moved manually back and forth. The X-ray irradiation angle corresponding to the back-and-forth position is calculated depending on the position data detected by a tomography mechanism position detection means 20. The preparation is thus completed and the control enters the radiographing sequence.

Figure 16:
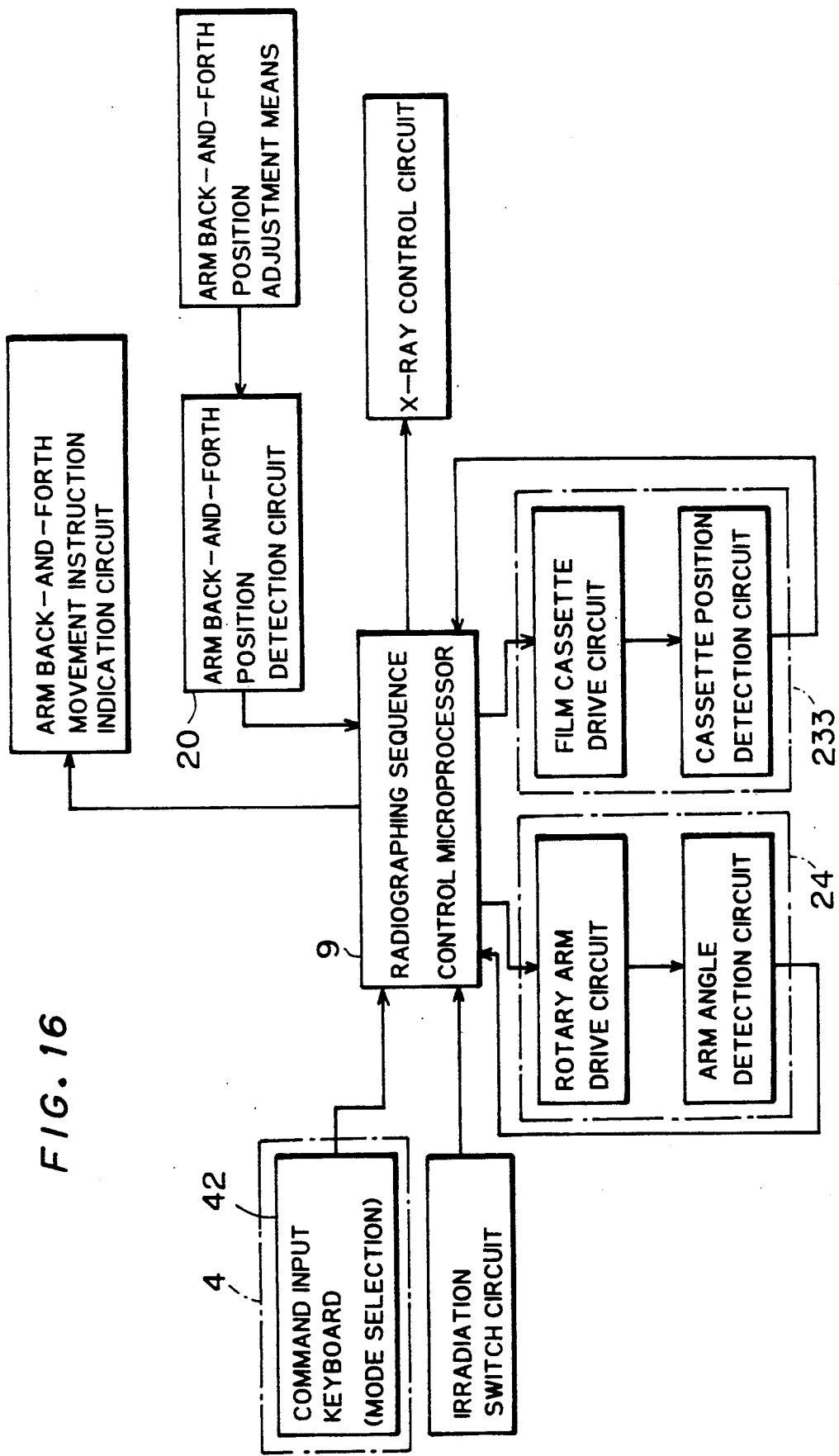
FIGS. 16 and 17 are block diagrams of the circuitry for the radiographing sequence.
Figure 17:
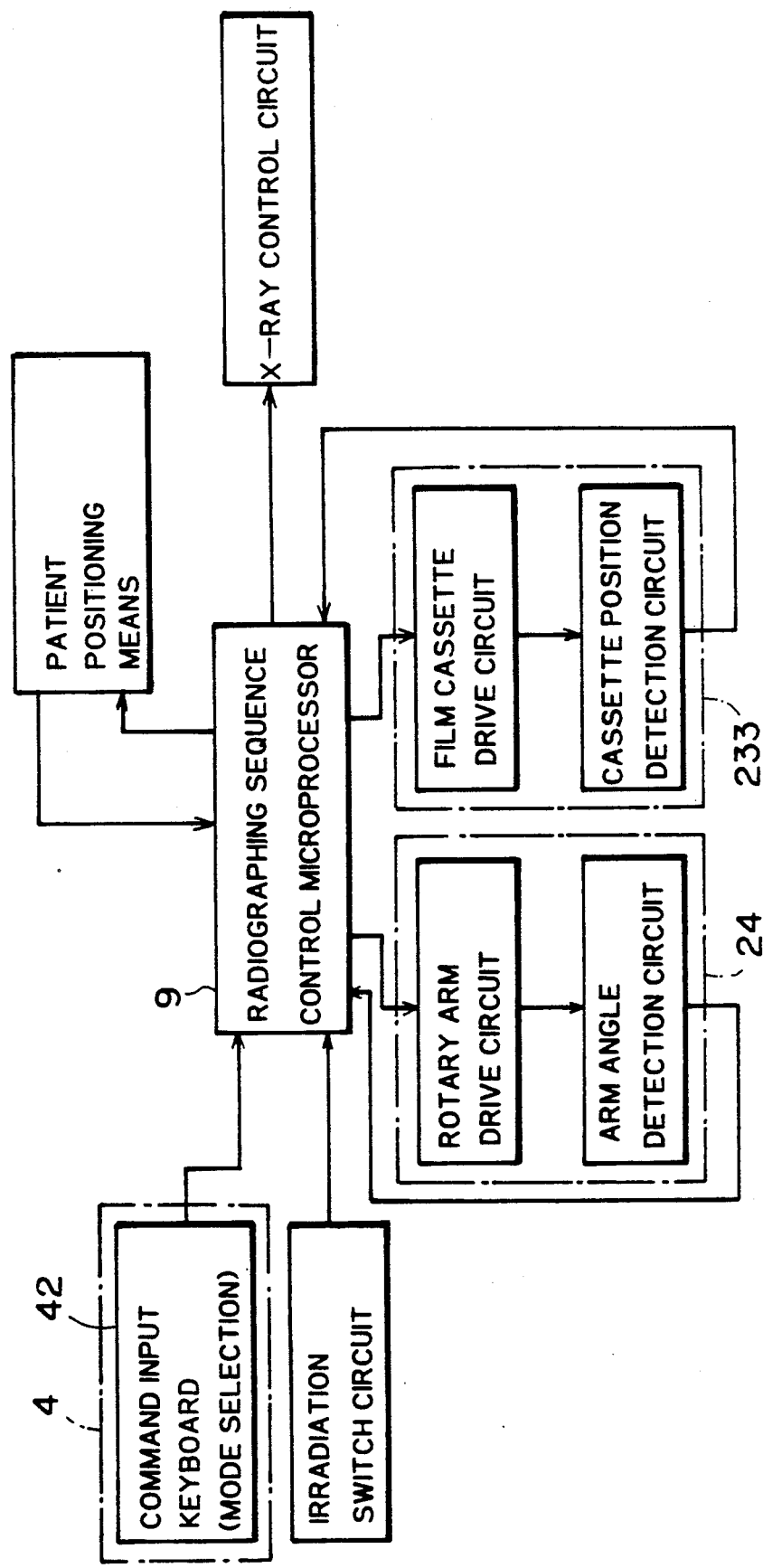

FIGS. 16 and 17 are block diagrams of the circuitry for the radiographing sequence.

FIG. 16 shows an example wherein positioning is performed manually. A radiographing sequence control microprocessor 9 receives a selection command signal from the radiographing mode selection means 4 and determines the radiographing sequence suited for the selected radiographing mode. After the rotary arm 21 is moved back and forth manually, the position of the rotary arm 21 is detected by the tomography mechanism position detection means 20 and input to the microprocessor 9. The position is indicated by an indication circuit. The microprocessor 9 issues command signals to the rotary arm drive mechanism 24 (drive circuit and arm angle detection circuit) and the X-ray film moving mechanism 233 (drive circuit and position detection circuit) to determine the rotation pattern of the rotary arm 21 and the movement pattern of the X-ray film 231. In addition, a command signal is also issued to the X-ray control circuit to determine the proper X-ray irradiation timing. When the X-ray irradiation switch is turned on, the radiographing sequence corresponding to the selected radiographing mode is executed.

FIG. 17 shows an example wherein positioning is performed automatically. The information from the automatic patient positioning means is input to the microprocessor 9. The commands from the microprocessor 9 are used to execute the radiographing sequence.

Figure 18:
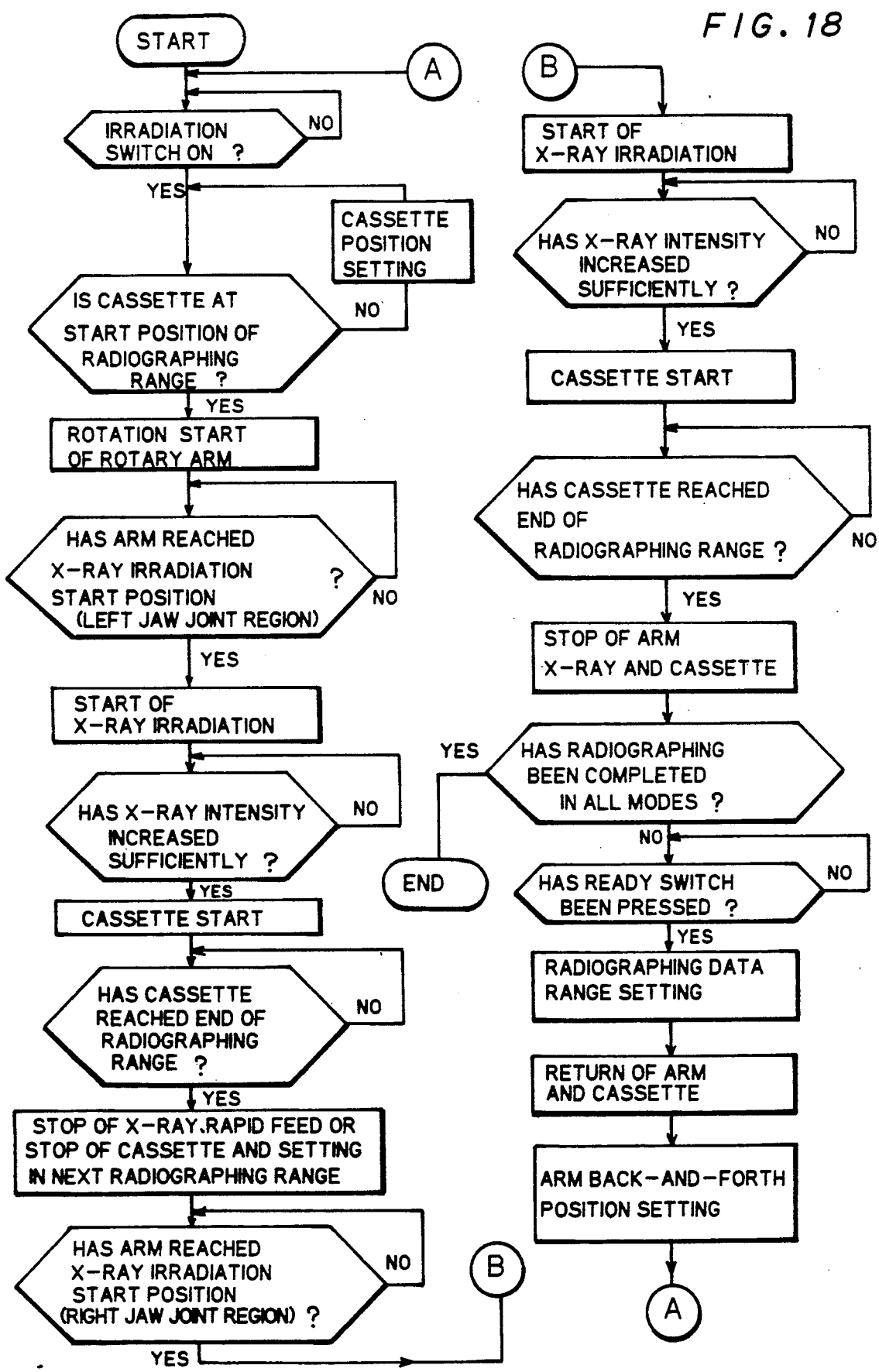
FIG. 18 is a flowchart of the radiographing sequence.

FIG. 18 is a radiographing sequence flowchart wherein divided images of jaw joints are mainly taken using the radiographing device including the patient positioning means. Referring to FIG. 18, while the irradiation switch is turned on after start, checking is performed to find out whether the film cassette 234 has been set at the start position in the radiographing range or not. If the cassette 234 has not been set properly, it is set properly. The rotary arm 21 begins to rotate. When the rotary arm 21 reaches the X-ray irradiation start position (for example, the left jaw joint region), the X-ray begins to be irradiated. After the sufficient increase of the intensity of the X-ray is confirmed, the film cassette 234 begins to be fed and the irradiation region is radiographed. When the film cassette 234 reaches the end position of the radiographing range, the position is checked to confirm that the film cassette 234 has reached the end position. After the confirmation, X-ray irradiation stops and the film cassette 234 is fed rapidly or stopped and set at the next radiographing range. The rotary arm 21 further rotates. When the rotary arm 21 reaches the next X-ray irradiation start position (for example, the right jaw joint region), the position is checked and corrected. X-ray irradiation then begins. After the sufficient increase of the intensity of the X-ray is confirmed, the film cassette 234 begins to be fed in the same manner as described above. When the rotary arm 21 reaches the end position of the radiographing range, the rotation of the rotary arm 21, X-ray irradiation and the feeding of the film cassette 234 are stopped. A confirmation is done to check that radiographing in all radiographing modes (for example, the above-mentioned radiographing modes at different X-ray irradiation angles) has been ended. If ended, the radiographing sequence is completed. If not, the radiographing range data is set under the condition that the ready switch has been pressed. The rotary arm 21 and the film cassette 234 return. After the back-and-forth position of the rotary arm 21 is set, the rotary arm 21 returns to its start position. Another radiographing sequence is executed according to the conditions in different radiographing modes. The above-mentioned radiographing sequence is also executed in the case of the panoramic radiographing and otolaryngological region radiographing modes, although some changes are necessary. If the automatic positioning mechanism is not included, the sequence needs to be changed accordingly.

The tomography mechanism 2 which is movable back and forth is mainly described in the above-mentioned embodiment. However, the patient positioning means 3 which is movable back and forth can be included in the embodiment. In addition, both the tomography mechanism 2 and the patient positioning means 3 which are movable back and forth can also be included in the embodiment.

As described above, the medical panoramic radiographing device of the present invention has jaw joint and/or otolaryngological region radiographing functions as well as panoramic radiographing functions which are inherent thereto. The X-ray irradiation timing and the X-ray film movement pattern of the device are systematically determined depending on the selected radiographing mode. Therefore, unlike the jaw joint or otolaryngological region radiographing operation using a conventional panoramic radiographing device, the radiographing patterns can be selected and set very easily and accurately without requiring any troublesome operations and without being affected by any differences among individual operators. If the tomography mechanism 2 and/or the patient positioning means 3 are made movable back and forth and if different X-ray irradiation angles are selectable in the jaw joint or otolaryngological region radiographing mode, various images of the portions to be radiographed can be obtained and more valuable diagnosis information can be provided. In this way, the device of the present invention is regarded as a general-purpose and versatile medical panoramic radiographing device equipped with superior functions. The device is thus very valuable in practical applications.

We claim:

1. A medical panoramic radiographing device comprising a panoramic radiographing main body (1), a horizontal rotary arm (21) which is supported by the main body (1) to rotate horizontally, an X-ray source (22) which is held at one end of said arm (21), an X-ray film holder (23) which includes an X-ray film (231) and is held at the other end of said arm (21) in an opposed relation with respect to said X-ray source (22), an X-ray tomography mechanism (2) which irradiates an X-ray beam from the X-ray source (22) to the X-ray film (231) in a substantially perpendicular direction while the movement speed of the X-ray source (22) is synchronous with that of the X-ray film (231) as the rotary arm (21) rotates, and a patient positioning means (3) which is disposed between the X-ray source (22) and the film holder (23), said medical panoramic radiography device being characterized in that said medical panoramic radiographing device further comprises a radiographing mode selection means (4) which is used to select a panoramic radiographing mode or jaw joint radiographing mode otolaryngological region radiographing mode, an X-ray irradiation timing determination means (5) which is used to determine an X-ray irradiation timing appropriate to the rotation position of the rotary arm (21) in the radiographing mode selected by said selection means (4), and an X-ray film movement pattern determination means (6) which is used to determine the movement pattern regarding said movement timing and speed of the X-ray film (231) in said radiographing mode selected by said selection means (4) and wherein:

said tomographing mechanism (2) and/or the patient positioning means (3) are movable back and forth by a moving mechanism (7) and said moving mechanism (7) is activated in said radiographing mode selected by said radiographing mode selection means (4);

the appropriate movement distance of said moving mechanism (7) to be activated in said radiographing mode selected by said radiographing mode selection means (4) is determined by a back and forth movement distance determining means (8); and said back and forth movement distance determination means (8) compares the detection position data detected by a position detection sensor (81), which detects the relative position of the dental arch of the patient being held by said patient positioning means (3) to the panoramic radiographing main body (1), with the relative position data of the tomographic region drawn by said tomographing mechanism (2) to the panoramic radiographing main body (1), and issues a command signal to said moving mechanism (7).

2. A medical panoramic radiographing device according to claim 1, wherein said radiographing mode selection means (4) further includes a selection means (41) capable of selecting different X-ray irradiation angles in said jaw joint or otolaryngological region radiographing mode, and a command signal from said selection means (41) is input to said moving mechanism (7) or said back-and-forth movement distance determination means (8) to move said tomography mechanism (2) and/or the patient positioning means (3) back and forth to their predetermined positions.

3. A medical panoramic radiographing device according to claim 1, wherein a position detector (232) is provided on said X-ray film holder (23), and when divided images of jaw joints or otolaryngological regions are taken on the single X-ray film (231), said position detector (232) detects each movement distance of said X-ray film (231) and turns off X-ray irradiation to prevent the boundaries of said divided images from being overlapped.

* * * * *